United States Patent
Smola et al.

(10) Patent No.: US 9,849,079 B2
(45) Date of Patent: Dec. 26, 2017

(54) MEDICINAL SKIN PROTECTION COMPOSITION WITH AN ACTIVE INGREDIENT COMBINATION WHICH IMPROVES THE SKIN BARRIER

(75) Inventors: Hans Smola, Saarbruecken (DE); Marina Kagan-Hoper, Ulm (DE); Thomas Mangen, Duesseldorf (DE); Petra Allef, Essen (DE); Eckhard Heisler, Geldern (DE)

(73) Assignees: Paul Hartmann AG, Heidenheim (DE); Evonik Industrie AG, Krefeld (DE)

( * ) Notice: Subject to any disclaimer, the term of this patent is extended or adjusted under 35 U.S.C. 154(b) by 0 days.

(21) Appl. No.: 14/239,345

(22) PCT Filed: Aug. 10, 2012

(86) PCT No.: PCT/EP2012/065658
§ 371 (c)(1),
(2), (4) Date: Mar. 11, 2014

(87) PCT Pub. No.: WO2013/024012
PCT Pub. Date: Feb. 21, 2013

(65) Prior Publication Data
US 2014/0178458 A1    Jun. 26, 2014

(30) Foreign Application Priority Data

Aug. 18, 2011 (DE) .......................... 10 2011 110 909

(51) Int. Cl.
| | |
|---|---|
| A61K 9/00 | (2006.01) |
| A61K 9/70 | (2006.01) |
| A61K 36/55 | (2006.01) |
| A61K 31/401 | (2006.01) |
| A61K 31/198 | (2006.01) |
| A61K 31/4172 | (2006.01) |
| A61K 31/20 | (2006.01) |
| A61K 31/201 | (2006.01) |
| A61K 9/107 | (2006.01) |
| A61K 31/202 | (2006.01) |
| A61Q 19/00 | (2006.01) |
| A61L 15/34 | (2006.01) |
| A61L 15/40 | (2006.01) |
| A61L 15/44 | (2006.01) |
| A61K 8/36 | (2006.01) |
| A61K 8/44 | (2006.01) |
| A61K 8/49 | (2006.01) |
| A61K 8/92 | (2006.01) |
| A61K 36/736 | (2006.01) |

(52) U.S. Cl.
CPC ............ *A61K 9/0014* (2013.01); *A61K 8/361* (2013.01); *A61K 8/44* (2013.01); *A61K 8/4913* (2013.01); *A61K 8/4946* (2013.01); *A61K 8/922* (2013.01); *A61K 9/107* (2013.01); *A61K 9/7007* (2013.01); *A61K 31/198* (2013.01); *A61K 31/20* (2013.01); *A61K 31/201* (2013.01); *A61K 31/202* (2013.01); *A61K 31/401* (2013.01); *A61K 31/4172* (2013.01); *A61K 36/55* (2013.01); *A61K 36/736* (2013.01); *A61L 15/34* (2013.01); *A61L 15/40* (2013.01); *A61L 15/44* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 7,261,946 | B2 * | 8/2007 | Claude | 428/500 |
| 2004/0171765 | A1 * | 9/2004 | Tsuji et al. | 525/452 |
| 2006/0047095 | A1 * | 3/2006 | Pacetti | 526/242 |
| 2007/0259101 | A1 * | 11/2007 | Kleiner et al. | 427/2.24 |
| 2009/0082284 | A1 * | 3/2009 | Sorns et al. | 514/23 |
| 2012/0276172 | A1 * | 11/2012 | Zhao | 424/400 |

FOREIGN PATENT DOCUMENTS

| | | |
|---|---|---|
| DE | 10 2007 028027 | 12/2008 |
| DE | 10 2007 031452 | 1/2009 |
| WO | WO 2006/036557 | 4/2006 |

OTHER PUBLICATIONS

Chempro Top-Notch Technology in Production of Oils and Fats. May 26, 2010.*
http://www.cosdna.com/eng/cosmetic_368929440.html.*
Ghadially R et al, Journal of Clinical Investigation (May 1995) vol. 95 (5), pp. 2281-2290.
Visscher M et al., Journal of Cosmetic Science (Jan. 2003) vol. 54(3), pp. 289-300.
Mohammad Najmul Ghani Khan, Khazaain-al-Advia vol. I, 05 (p. 04-08), ( Ref.pg. no.of publication:692 ), 1911 AD (20th century AD), Nadeem Yunus Printer /Sheikh Mohd Basheer & Sons, Lahore.†

(Continued)

*Primary Examiner* — Robert A Wax
*Assistant Examiner* — Danah Al-Awadi
(74) *Attorney, Agent, or Firm* — Chalin A. Smith; Smith Patent LLC (57) ABSTRACT

A medicinal skin protection composition is disclosed with an active ingredient combination that specifically serves to care for aging skin that is exposed to difficult environmental conditions. The active ingredient combination obligatorily includes the components almond oil, linseed oil fatty acids, amino acids, and creatine. The medicinal skin protection composition can be used for aging skin in the form of creams, lotions etc., and also for a variety of incontinence articles, such as sanitary towels or nappies.

26 Claims, 7 Drawing Sheets

(56) References Cited

OTHER PUBLICATIONS

Abu Ali Ibn-e-Sina, Al-Qaanoon-fil-Tibb vol. II, 05 (p. 09-13), ( Ref.pg. no.of publication:76 ), 1987 AD (11th century AD), Institute of History of Medicine and Medical Research Jamia, Hamdard, New Delhi-62, India.†

Abu Ali Ibn-e-Sina, Al-Qaanoon-fil-Tibb vol. II, 5 (p. 14-18), ( Ref.pg. no.of publication:80 ), 1987 AD ( 11th century AD), Institute of History of Medicine and Medical Research Jamia, Hamdard, New Delhi-62, India.†

\* cited by examiner
† cited by third party

GIBCO 1:500

Linseed FS 100 µM

MEDICINAL SKIN PROTECTION COMPOSITION WITH AN ACTIVE INGREDIENT COMBINATION WHICH IMPROVES THE SKIN BARRIER

PRIORITY

This application corresponds to the national phase of International Application No. PCT/EP2012/065658 filed Aug. 10, 2012 which, in turn, claims priority to German Patent Application No. 10 2011 110 909.2 filed Aug. 18, 2011, the contents of which are incorporated by reference herein in their entirety.

FIELD OF THE PRESENT INVENTION

The present invention relates to compositions containing an active ingredient combination of almond oil, linseed oil fatty acids, amino acids, and creatine, for use for medicinal-dermatologic purposes. The compositions are suitable for cleaning, care, and protection of the human skin, in particular barrier-damaged skin.

BACKGROUND OF THE INVENTION

With increasing age the skin has a growing imbalance between the build-up and degradation of collagen, one of the main constituents of the dermis, towards the degradation. This is inter alia due to a low rate of newly synthesized collagen and an increased activity of collagen-degrading enzymes, such as collagenase MMP-1. Moreover, the capability of the skin for regeneration decreases with increasing age. Thus, mature skin, in particular, if it is exposed to adverse ambient influences such as pressure, lacking aeration or moisture, needs special care. Such adverse influences often occur with physical malfunctions, such as incontinence.

The products according to the invention above all provide people with barrier-damaged skin with a protecting and caring effect. The need for such products is in particular with so-called aging skin.

The concept of aging skin, i.e. the visible aging of the skin from the age of 50, in particular from the age of 65, is recognized by those in the art. It is understood to include both the natural, i.e. genetically programmed, so-called intrinsic aging or time aging, and the so-called extrinsic aging or light aging as a result of physical, chemical, and microbiological noxae. Skin aging is accompanied by a structural reduction of the skin, i.e. in all layers the skin becomes thinner and poorer in cells and function-bearing structures. Therefore, the barrier function of the skin is partially lost, see Hautkrankheiten und Hautpflege im Alter, O. P. Hornstein, Wissenschaftliche Verlagsgesellschaft mbH, Stuttgart, 2002.

Symptoms of aging skin are dry skin, refractory itching conditional on the dry skin (Norman R A. Geriatric dermatology. Dermatol Ther. 2003; 16:260-8) or also independently thereof, creases and pigment spots. Particularly, the dryness of the skin (xerosis) can lead to intensive pruritus (Norman R A. Xerosis and pruritus in the elderly: recognition and management. Dermatol Ther. 2003; 16:254-9) and, in particular cases can be perceived as sensitive skin. Recent works suggest that dry skin is associated with mutations in the filaggrin gen (Sergeant et al., Heterozygous null alleles in filaggrin contribute to clinical dry skin in young adults and the elderly. J Invest Dermatol. 2009 129:1042-5). In turn, filaggrin mutations have been associated with the Natural Moisturizing Factor, NMF (Kezic et al., Natural moisturizing factor components in the stratum corneum as biomarkers of filaggrin genotype: evaluation of minimally invasive methods. Br J Dermatol. 2009 161:1098-104) and may well explain dry skin and the accompanied barrier disruption. NMF is degraded by the degradation of filaggrin into amino acids that inter alia are further degraded into 2-pyrrolidone-5-carboxylic acid (PCA) and urocanic acid (UCA) in the corneum. If the aminogram of profilaggrin (NCBI Reference Sequence: NP_002007.1) is considered from which filaggrin is generated by proteolysis in the uppermost skin layers, specific differences over human serum albumin (NCBI Reference Sequence: NP_000468.1) in the relative distribution of the amino acids contained therein stand out. NMF, but also amino acids, are reduced by washing procedures or occlusion and are newly formed in the recovery phase (Robinson et al., Natural moisturizing factors (NMF) in the stratum corneum (SC). I. Effects of lipid extraction and soaking. J Cosmet Sci. 2010 61:13-22. Robinson et al., Natural moisturizing factors (NMF) in the stratum corneum (SC). II. Regeneration of NMF over time after soaking. J Cosmet Sci. 2010 61:23-9. Visscher et al., Regional variation in the free amino acids in the stratum corneum. Int J Cosmet Sci. 2010 61:303-9. Visscher et al., Stratum corneum free amino acids following barrier perturbation and repair. Int J Cosmet Sci. 2011 33:80-9).

DE 10 2007 031 452 discloses moisturizing cosmetic and dermatologic compositions with a combination of various enhancers that markedly improve the effect of conventional humectants from the outside for the treatment of dry skin. Moreover, this publication lists an almost immense amount of different additional additives.

US 2008/0193393 discloses an administration system for topically applied components, wherein this system obligatorily contains a fatty acid, a phospholipid, and an oil in a specific ratio of weight percentages to one another.

US 2008/0268077 discloses a method for enhancing the barrier function of damaged skin wherein a mixture of a ceramide and/or a pseudo-ceramide together with an active ingredient effective against skin irritations, such as bisabolol, panthenol, ginger extracts, and mixtures thereof, is to be used.

US 2010/0286102 describes cosmetic or pharmaceutical formulations for skin or hair that contain one or more ceramides and/or pseudo-ceramides and (alpha-)bisabolol.

Ghadially et al., The Journal of Clinical Investigation, Inc. (1995), p. 2281-2290, describe the barrier function of the human skin. With increasing age human skin becomes more problematic in comparison to the young skin in view of the regeneration of the barrier function after irritations. This is shown in a provocation of the skin with a solvent (acetone) as well as in mechanical irritations (adhesive strip test).

Against this background, skin care in old age, in particular skin care of immobile and/or people suffering from urinary and/or fecal incontinence and/or decubitus and other wound diseases represents a particular challenge.

SUMMARY OF THE INVENTION

The aim of skin care in old age is to regenerate and enhance the decreasing barrier function of the skin. Moreover, the accompanying symptoms such as dry skin and itching or skin irritations are to be reduced. This is especially necessary if the skin in immobile and/or people suffering from urinary and/or fecal incontinence and/or decubitus and other wound diseases on the one hand is only capable of a reduced physiological regeneration for example due to a reduced circulation and on the other hand the skin additionally is exposed to negative influences by the climate associated with carrying incontinence products.

According to the invention medicinal skin protection compositions for an improved skin care in old age are provided that include an active ingredient combination containing almond oil, linseed oil fatty acids, amino acids, and creatine in a dermatologically acceptable carrier. Here, the composition considers physiological aspects. A medicinal skin protection composition according to the invention comprises:

an active ingredient combination according to the invention for care of aging skin that consists of the following components:
  a) 0.01 to 20% by weight almond oil,
  b) 0.01 to 1.5% by weight linseed oil fatty acids,
  c) 0.001 to 0.5% by weight amino acids, and
  d) 0.01 to 1.5% by weight creatine,
wherein the given weight percentages each relate to the total composition of the end product.

In preferred embodiments, the active ingredient combination consists of 0.05 to 18% by weight, further preferred of 0.1 to 15% by weight of almond oil and particularly preferred of 0.1 to 6% by weight of almond oil; 0.02 to 1.2% by weight, preferably 0.05 to 0.8% by weight of linseed oil fatty acids and particularly preferred of 0.1 to 0.7% by weight of linseed oil fatty acids; 0.002 to 0.3% by weight, preferably 0.005 to 0.15% by weight of amino acids and particularly preferred of 0.05 to 0.1% by weight of amino acids, and 0.02 to 1.2% by weight, preferably 0.05 to 0.8% by weight of creatine and particularly preferred of 0.1 to 0.75% by weight of creatine, wherein the weight percentages each relate to the total composition of the end product. The components of the end product add to 100% by weight.

The active ingredient combination according to the invention is intermingled into products that are medicinal skin protection compositions for topical application. In addition to the active ingredient combination according to the invention such end products contain further ingredients, as they are common in compositions for topical application. These include for example oil components, emulsifiers, solubilizers, preservatives, antioxidants, viscosity and pH regulators, dyes and fragrances as well as water. With these ingredients the active ingredient combination according to the invention adds to 100% by weight of the total composition. Here, it is not necessary that the individual components of the active ingredient combination according to the invention are first put together or mixed, respectively, but according to the requirements of the production method the individual components together with the other ingredients can also be intermingled into the products one after the other or optionally as mixtures of two or three components.

Alternatively, the medicinal skin care composition for care of aging skin according to the invention includes an active ingredient combination of the following components:
  a) 0.1 to 15% by weight of almond oil,
  b) 0.05 to 0.8% by weight of fatty acids of vegetable origin with an omega6 to omega3 fatty acid ratio of 1 to >1,
  c) 0.005 to 0.15% by weight of amino acids selected from one or more of the amino acids arginine Arg, glutamine Gln, histidine His, and serine Ser and/or at least one natural moisturizing factor, preferably pyrrolidine carboxylic acid PCA and/or urocanic acid UCA,
  d) 0.05 to 0.8% by weight of creatine.

In a preferred embodiment, an active ingredient combination according to the invention includes almond oil having a content of about 70-80% of oleic acid, 10-20% of linoleic acid as well as 5-10% of palmitic acid and optionally also subordinated residues of other acids.

DETAILED DESCRIPTION OF THE PREFERRED EMBODIMENTS

Almond oil is a fatty oil that is recovered by cold-drawing or extraction and subsequent refining from sweet almonds of the almond tree (*prunus amygdalus dulcis*). The almond oil mainly consists of triesters of the glycerin. Since the oil has a very high proportion of unsaturated fatty acids it quickly becomes rancid and is light sensitive. In order to prevent rancidification of the product the almond oil has to be protected from oxidation by atmospheric oxygen as well as light. Thus, in processing it is advantageous to work under nitrogen atmosphere or antioxidants have to be added that are suitable with respect to skin tolerance.

A further essential constituent of the active ingredient combination according to the invention is linseed oil fatty acids. Linseed oil is a vegetable oil recovered from linseed. Essential free fatty acids of vegetable origin with an omega6 to omega3 ratio of 1 to >1 (e.g. according to http://efaeducation.nih.gov/sig/esstable.html last called up on Sep. 8, 2011) are to provide the skin with essential fatty acids, wherein the release from triglycerides should be avoided for reasons of bioavailability. Therefore, absorption of free essential fatty acids can be via fatty acid transport protein-1, -2, -3, -4, -5, -6 or fatty acid translocase/CD36 (summarized in Feingold. Thematic review series: skin lipids. The role of epidermal lipids in cutaneous permeability barrier homeostasis. J Lipid Res. 2007 48:2531-46).

It is the aim to reduce the pro-inflammatory effect of omega6 fatty acids by selecting suitable starting materials. Moreover, some free fatty acids have a growth inhibiting effect on pathogenic bacteria (review in Desbois et al., Antibacterial free fatty acids: activities, mechanisms of action and biotechnological potential. Appl Microbiol Biotechnol. 2010 85:1629-42) that can disturb the physiology of the skin. Together with the anti-inflammatory properties of the fatty acid mixture by a high proportion of omega3 a synergistic activity is achieved from normalizing the skin flora and low inflammatory activity of the skin. For this synergistic effect, the administration form has to be ensured in the form of free fatty acids and not as fatty acid triglyceride.

By linseed oil fatty acids (INCI: linseed acid, CAS: CAS 68424-45-3, EINECS No. 270-307-6) free fatty acids are understood that are recovered from linseed oil that is pressed out of the seeds of flax cold or hot under pressure. According to the sort and origin of the linseed and the method of oil recovery the natural composition of the linseed oil and the linseed oil fatty acids recovered therefrom varies. The fatty acid mixture recovered from linseed contains saturated and mono- and polyunsaturated fatty acids and is characterized by the high content of omega3 fatty acids. The linseed oil fatty acids used in the active ingredient combination according to the invention have a ratio of omega6 to omega3 fatty acids of 1 to >1, preferably of 1 to >2, preferably of 1 to >2.5, preferably of 1 to ≥3 and preferably of at most 1 to 5.

In addition, by linseed oil fatty acids such fatty acid mixtures are understood that are of a different natural, in particular vegetable origin and a have a ratio of omega6 to omega3 fatty acids of 1 to >1. This comprises active ingredient combinations based on vegetable oils with a low proportion of omega3 fatty acid, such as for example hempseed oil (omega6 to omega3: approx. 3:1), rapeseed oil (2:1), or soybean oil (7:1) and that are enriched with omega3 fatty acids to achieve a ratio of omega6 to omega3 fatty acids of 1 to >1. Omega-3 means that the last double bond in the polyunsaturated carbon chain of the fatty acid is present at the third-last carbon-carbon bond, as seen from the carboxy end. Correspondingly, the omega-6 fatty acids at the sixth position have the first double bond, as seen from the omega end.

Preferably, the linseed oil fatty acids are a mixture of the following fatty acids (number of C atoms:number of double bonds in brackets) each given in the relative proportions:
palmitic acid (C16:0) 4-8%,
stearic acid (C18:0) 2-5%,
oleic acid (C18:1) 16-26%,
linoleic acid (C18:2) 14-24%,
linolenic acid (C18:3) 43-55% as well as
fatty acids with carbon chains having more than 18 carbon atoms 0.1-2%;
wherein the percentages add up to 100%.

The content of omega3 fatty acids in the form of linolenic acid is 43-55%, the content of omega6 fatty acids in the form of linoleic acid is 14-24% (each based on the total linseed oil fatty acid component), the ratio of omega6 to omega3 fatty acids is 1:2 to 1:4.

A preferred linseed oil fatty acid component can be obtained under the name "Cremerac Polyungesättigte Fettsäuren Destillierte Leinölfettsäure" by Cremer Oleo GmbH & Co. KG, Hamburg.

The free fatty acids have an anti-microbial activity. They support the skin's natural flora in the maintenance of the skin's acid mantle. The improvement of the barrier effect of the active ingredient complex on the aging skin is substantially caused by the linseed oil fatty acids. This is shown in an in vitro reconstruction of human epidermis. The transfer of the effect observed in the in vitro model on the application with aging skin results in the formation of a compact skin structure that is advantageous to allow a supply of the outer skin layers with moisture from the inside.

If the in vitro reconstructed human epidermis is exposed to a detergent a significant loss of viability of the cells (>50%) that are well-differentiated in the standard growth medium is observed after 240 minutes, whereas the cells from a linseed oil fatty acid-containing growth medium are much more robust over the detergent and do not show a significant reduction of the viability, even not after 360 minutes. The viability of the cells from a linseed oil fatty acid-containing growth medium is increased by 50% over cells from a standard growth medium.

A further component of the active ingredient combination represents 0.005 to 0.15% by weight of amino acids. Amino acids are of great importance for the skin, since on the one hand they can effectively store water and thus are relevant for the regulation of the skin moistness and on the other hand serve as natural protection of the skin against free radicals.

In a preferred embodiment the amino acid component contains at least one or more of the amino acids arginine Arg, glutamine Gln, histidine His, and serine Ser and/or at least one natural moisturizing factor, preferably pyrrolidine carboxylic acid PCA and/or urocanic acid UCA. In a further preferred embodiment the amino acid component contains at least the amino acids arginine Arg, glutamine Gln, histidine His, and serine Ser, preferably at least up to 15%, based on the proportion of the amino acids.

A supplementation with amino acids that considers the specific composition of profillagrin and at least contains the amino acids arginine Arg, glutamine Gln, histidine His, serine Ser, and pyrrolidine carboxylic acid PCA as precursor and constituents of the NMF is particularly preferred. Also, preferably a factor of the NMF should already be present in the active form such as, e.g. pyrrolidine carboxylic acid PCA (2-pyrrolidone-5-carboxylic acid) and/or urocanic acid UCA.

Thus, it is particularly advantageous if the active ingredient combination according to the invention contains at least the amino acids arginine Arg, glutamine Gln, histidine His, serine Ser, and further preferred, in addition to said amino acids, pyrrolidine carboxylic acid PCA and/or UCA (urocanic acid). So, together with the free fatty acids the physiology of the skin surface is enhanced.

Further mainly essential amino acids can be supplemented that for the build-up and regeneration, respectively, of the epidermal barrier serve as topic nutrition (nutritive effect).

Preferably, the content of arginine, histidine, and serine in a mixture of amino acids is up to 20% (based on all amino acids of the mixture, corresponding to 100%). L-Arginine as metabolic urea precursor is also enriched in the corneum after its conversion to urea and thus results in a reduction of the dryness of the skin, however with the advantage that during the application of L-arginine to pre-damaged skin irritative side effects are avoided that can occur in the direct application of urea.

A preferred amino acid complex contains:

| | |
|---|---|
| L-arginine | 8.0% |
| L-aspartamic acid | 5.2% |

-continued

| | |
|---|---|
| L-pyrrolidone carboxylic acid | 4.27% |
| glycine | 1.28% |
| L-alanine | 1.2% |
| L-serine | 0.8% |
| L-valine | 0.64% |
| L-proline | 0.4% |
| L-threonine | 0.4% |
| L-isoleucine | 0.4% |
| L-histidine | 0.16% |
| L-phenylalanine | 0.16% |

It is available as a 50% aqueous solution (further ingredients 15% sodium L-pyrrolidone carboxylate, 12% sodium lactate) under the name "Prodew 500" of Ajinomoto Co., Inc., Tokyo, Japan.

The fourth component of the active ingredient combination according to the invention is 0.05 to 0.8% by weight, based on the finished total composition, of creatine. Creatine is an organic acid that is synthesized in the human body in the kidney, liver, and pancreas. Creatine acts together with the other constituents of the active ingredient combination and improves the caring activity of the products.

Creatine can be added to the formulation, in particular when the inflammatory reaction of skin cells by oxidative stress or other causes is to be reduced (Lenz et al., The creatine kinase system in human skin: protective effects of creatine against oxidative and UV damage in vitro and in vivo. J Invest Dermatol. 2005 124:443-52). This concept is particularly practical, when the formulation contains both creatine and free fatty acids of low pro-inflammatory potential in combination, as is the case with a low content of omega6 fatty acids. This is particularly desired in skin protection products.

A medicinal skin protection composition according to the invention contains an active ingredient combination as described. The respective given proportions of the individual components of the active ingredient combination as weight percentage relate to the total composition. Of course, the individual components of the active ingredient combination together with the remaining constituents of the medicinal skin protection composition always add to 100% by weight.

In a further preferred embodiment the medicinal skin protection composition according to the invention only includes the respective components of the active ingredient combination in the given weight percentages as well as further excipients required for the stability and function of the composition. If there are only preferred representatives of the individual components present, preferably no further less preferred representatives of the respective components are added. In these preferred embodiments then the medicinal skin protection compositions include only the preferred representatives of the respective components, but no further less preferred representatives of these components. In such preferred cases the active ingredient combination consists only of the respective preferred representatives of these components.

Preferably, the active ingredient combination according to the invention is intermingled into a medicinal skin protection composition that is present as water-in-oil emulsion (W/O) or water-in-oil-in-water emulsion (W/O/W). In a particularly preferred embodiment, the compositions according to the invention are lotions, creams, and foams that in addition to the other common constituents of a topic composition include the active ingredient combination according to the invention.

In the formulation of the medicinal skin protection compositions it must be considered that the skin physiology of the aging skin is taken into account. Therefore, the compositions have a pH value between 4.0 and 6.5, in particular between 4.5 and 6.0 and further in particular between 4.8 and 5.1.

A pH value that orients towards the different needs of the skin physiology ranges from pH 4.0 to pH 6.5. pH 4.0 if an optimized biochemical synthesis and processing performance of the corneum is desired (Hachem et al., Acute acidification of stratum corneum membrane domains using polyhydroxyl acids improves lipid processing and inhibits degradation of corneodesmosomes. J Invest Dermatol. 2010 130:500-10). pH 6.5 if, e.g. in the inguinal area an adapted formulation is desired (in Altmeyer Ed., Therapielexikon Dermatologie und Allergologie. p. 695, 2. ed. 2005, Springer Verlag Berlin Heidelberg). In this context, works are of importance that could show that the surface pH value of the skin in later years is markedly different from young skin (Choi et al., Stratum corneum acidification is impaired in moderately aged human and murine skin. J Invest Dermatol. 2007 127:2847-56). It has also been shown that other diseases can affect the pH value of the skin (Yosipovitch et al., Skin surface pH in intertriginous areas in NIDDM patients. Possible correlation to candidal intertrigo. Diabetes Care. 1993 16:560-3). From this derives the necessity for an adapted pH value adjustment of the products.

The four constituents of the active ingredient combination, namely almond oil (a), linseed oil fatty acids (b), amino acids (c), and creatine (d) in accordance with the invention are present in certain ratios to one another. The proportion of the active ingredient combination in the total composition can vary depending on the respective product. Not least, the respective proportion of the active ingredient combination depends on the intended purpose of use of the finished product. In highly stressed skin the content of the active ingredient combination can be higher than in less stressed skin. The proportion of the active ingredient combination in the total composition is between 0.001 and 25% by weight, preferably between 0.01 and 20% by weight, further preferred between 0.1 and 18% by weight and particularly preferred between 1.0 and 18.0% by weight.

In a preferred embodiment of the present invention the active ingredient combination is intermingled into a W/O emulsion in the form of a body lotion in a proportion of 1.0 to 25% by weight, preferably 2.5 to 20% by weight, further preferred 5.0 to 18% by weight and the ratio of amino acids:linseed oil fatty acids:creatine:almond oil is in the range of 0.5:2:4:100 to 0.5:4:5:100.

In a preferred embodiment of the present invention the active ingredient combination is intermingled into a W/O emulsion in the form of a skin protection cream and the ratio of the components amino acids:linseed oil fatty acids:creatine:almond oil is between 0.5:4:6:10 and 0.5:4:5:27 and the proportion of these components in the total composition is from 0.5 to 8.0% by weight, preferably from 0.75 to 7.0% by weight, further preferred from 1.0 to 6.0% by weight. The skin protection cream preferably has a content of zinc oxide of from 15 to 25% by weight, preferably 18 to 23% by weight.

In a preferred embodiment of the present invention the active ingredient combination is intermingled into a transparent skin protection cream that is present in the form of a W/O/W emulsion. The active ingredient combination is present in a content of from 0.05 to 2.0% by weight, preferably 0.1 to 1.7% by weight, further preferred from 0.2 to 1.3% by weight, based on the total composition of the transparent skin protection cream, wherein the ratio amino acids:linseed oil fatty acids:creatine:almond oil ranges from 0.5:1:1:2 to 0.5:1:1:5. The transparent skin protection cream is free from zinc oxide and forms a transparent protective film on the skin.

In another preferred embodiment the present invention relates to a foam having 0.1 to 4.0% by weight, preferably 0.2 to 3.5% by weight, further preferred 0.3 to 3.0% by weight of the active ingredient combination, based on the finished total composition. The individual components amino acids:linseed oil fatty acids:creatine:almond oil are in the range of from 0.0125:1:1:1 to 0.125:1:1:1. To generate such a foam, the liquid phase is placed in a spray can. In use, the liquid is foamed by means of the propellant and the caring foam is applied to the affected parts of the body.

The medicinal skin protection compositions according to the invention with an active ingredient combination in the topical application result in a protective effect against aqueous harmful substances. In the visual evaluation of the tested skin markedly less skin damages occur than in untreated skin. The barrier function of the skin can be better maintained by the topical application of the active ingredient combination according to the invention. A barrier damage of the skin that results in an increased vaporization of water through the uppermost skin layers is reduced. The change in trans-epidermal water loss (TEWL) of the skin with the active ingredient combinations according to the invention of treated skin is below the reference value of from 11 $g/hm^2$ for untreated skin exposed to aqueous harmful substances, preferably below 10 $g/hm^2$, in particular between 3 $g/hm^2$ and 9 $g/hm^2$.

Also an object of the invention is the use of a medicinal skin protection composition with the following components:
a) 0.001 to 40% by weight of almond oil,
b) 0.001 to 5.0% by weight of fatty acids of vegetable origin with an omega6 to omega3 fatty acid ratio of 1 to >1,
c) 0.001 to 1.0% by weight of amino acids, and
d) 0.001 to 5.0% by weight creatine,
for the topical application to aging skin.

A further object of the invention is the use of the medicinal skin protection compositions according to the invention that contain the active ingredient combinations for the topical application to aging skin.

The use is in particular on aging skin strained by bed confinement and/or urinary and/or fecal incontinence and/or decubitus and other wound diseases.

The topical application is for cleaning, caring, and protecting the aging skin, in particular of skin strained by carrying incontinence products or perilesional skin. Here, the compositions are designed body region-specific, i.e., they are adapted to the application to the whole body and/or to perilesional skin and/or the genitals, in particular genitals strained by incontinence. Genitals comprise the lower abdominal and the lower back area, in particular the genital and anal area and the perineum.

The transparent skin protection cream and the foam are indicated as barrier protection in the genitals, in particular in incontinence, after each intimate cleaning or caring. The application is to cleaned and intact skin by uniform distribution of the products in the genitals. For that, the foam is well shaken before use and preferably sprayed on a glove or another means for applying the foam. The dosage is in a pea- to hazelnut-sized amount.

The body lotion is indicated as intensive care after washing, showering or bathing, wherein the application is uniformly distributed to the whole body and the dosage is individually adapted to the body size and the skin condition.

The use is on the aging skin, preferably in combination with the use of absorbing healthcare products, in particular incontinence articles, primary wound dressings, and patient under pads.

The skin protection compositions according to the invention have a positive influence on the quality of incontinence products, confirmed in run-off tests as well as measures of the soak in times and rewetting. By the use of the medicinal skin protection compositions according to the invention in combination with incontinence articles the rewetting properties of the incontinence products are positively influenced so that there is almost completely no rewetting. In turn, this positively affects the skin condition of those parts of the body that come into contact with the incontinence article.

In another embodiment moreover it may prove practical and suitable to formulate the active ingredient combination in oral administration forms, for example as dragée or tablet as end product, for example in the form of a nutrient supplement. The effect on the skin is not topical, but after oral administration from the inside and can be in addition or as an alternative to an external application of the medicinal skin protection composition.

In a further embodiment the medicinal skin protection composition with an active ingredient combination as described above is present in the form of a coating that is applied to the sheet of absorbing healthcare articles that faces the skin of the user. Incontinence articles such as nappies, nappy pants, sanitary towels etc. on the side facing the skin of the user have a covering (fleece) layer causing the separation between the absorbing material (for example various polyacrylates) from the body surface.

It is known to in particular provide the skin-facing sheet of absorbing healthcare articles, that is, in particular the so-called top sheets, with reviving agents that positively affect the skin's health and at the same time do not negatively influence the absorption behavior of the healthcare article.

In the preparation of such healthcare products the medicinal skin protection composition with an active ingredient combination is applied either as a mixture or the individual components are applied sequentially to the fleece layer, for example by spraying. The medicinal skin protection composition with an active ingredient combination is preferably applied with an inert carrier phase. Here, the ratios of the individual components according to the invention to one another, as given for lotions and creams, are met and the amount of the active ingredient combination, based on the covering layer, ranges in an amount of from 0.01 to 20% by weight, based on the coated covering layer.

In this way, the performance characteristics of the absorbing healthcare article are not negatively influenced. Rather the use of the active ingredient combination in a reviving agent for an absorbing healthcare article, preferably an incontinence article, reduces rewetting. At the same time, the skin barrier function in those skin areas is enhanced, where the carrier of the absorbing healthcare article comes into contact with the absorbing healthcare article provided with an active ingredient combination-containing reviving agent, preferably an incontinence article.

EXAMPLES

The invention is explained in more detail by the following examples, wherein the components of the active ingredient combination, as well as all the other ingredients are commercial starting materials for topical compositions.

Example 1

Formulation 1: Body Lotion (W/O Emulsion)

| | | | |
|---|---|---|---|
| Aqua (Water) | 50-70 | % | solvent |
| Isopropyl Myristate | 5-15 | % | plasticizing/regreasing/distributing agent |
| Caprylic/Capric Triglyceride | 5-15 | % | oil component/regreasing agent |
| *Prunus Amygdalus Dulcis* (Almond) Oil | 5-15 | % | plasticizer, moisturizer/care component |
| Glycerine 85% | 0.5-5 | % | moistener/moisturizer |
| Cetyl PEG/PPG-10/1 Dimethicone | 0.5-5 | % | emulsifier |
| Potassium Sorbate | 0.1-0.8 | % | preservative |
| Sodium Benzoate | 0.1-0.8 | % | preservative |
| Citric Acid | 0.4-0.9 | % | pH regulator |
| Sodium Hydroxide | 0.2-0.8 | % | pH regulator |
| Creatine | 0.2-0.8 | % | moisturizer |
| Sodium Chloride | 0.2-0.8 | % | viscosity increasing agent |
| Hydrogenated Castor Oil | 0.2-0.8 | % | consistency factor |
| Cera Alba (beeswax) | 0.1-0.6 | % | consistency factor/plasticizer |
| Perfume (fragrance) | 0.1-0.6 | % | fragrance |
| Linseed Oil Fatty Acid | 0.1-0.6 | % | moisturizer/oil component |
| Amino Acid Complex | 0.05-0.15 | % | moistener/protein builder |
| Tocopherol | 0.01-0.04 | % | vit. E/antioxidant/moisturizer |
| *Rosmarinus Officinalis* (Rosemary) Leaf Extract | 0.005-0.015 | % | antioxidant |

The amounts of individual components are adjusted such that their sum yields 100% by weight.

Preparation of the Body Lotion:

a) Fatty Phase

Into the Fryma (homogenizer) the raw materials: almond oil, hydrogenated castor oil, caprylic/capric triglyceride, isopropyl myristate, cetyl PEG/PPG-10/1 dimethicone, bleached wax, distilled linseed oil fatty acid, rosemary extract, and mixed tocopherol concentrate are first added and heated to 85° C. At the stirrer adjustment of 10 rpm the temperature is maintained for about 15 minutes.

b) Water Phase

The Unimix is sterilized with ca. 150 kg water, subsequently it is cooled to 55° C. One part of hot water is let out for the pre-solutions: sodium chloride, citric acid are dissolved in the hot water. Sodium hydroxide solution, 50%, is dissolved in the hot water. Glycerine, 85%, amino acid complex are dissolved in the hot water. Potassium sorbate is dissolved in the hot water.

The pre-solutions are allowed to enter the Unimix at 30 rpm. The residual water, purified—except 10%—is allowed to enter the Unimix and is well stirred until a homogeneous solution is obtained (approx. 2 min./1400 r).

Then, creatine is allowed to enter and the remaining 10% purified water are also added. Homogenization within 2 min. at 1400 r. The pH value is controlled (set point 4.8-5.1).

c) Perfume Oil Phase

The perfume oil is weighted and provided.

d) Emulsification

The cold water phase is added into the Fryma to the hot fatty phase under stirring (20 rpm). Cooling is started with running stirrer (20 rpm). Homogenization: 2 Min./2200 r. Vacuum is released. At 35° C. the perfume oil is allowed to enter. It is homogenized for ½ min. at 700 r. Up to 27° C. it is cooled under stirring. Then, homogenization: 10 min./4000 r. Stirrer speed: 20 rpm. Vacuum is released. At 27° C. the lotion is pumped into a sterile storage tank by means of compressed air (ca. 1600 r).

Example 2

Formulation 2: Skin Protection Cream (W/O Emulsion)

| | | | |
|---|---|---|---|
| Aqua (Water) | 42-46 | % | Solvent |
| Zinc Oxide | 19-22 | % | Solid for covering and thus mechanical protection of the skin (skin protection agent) |
| Cethyl Ethyl Hexanoate | 6-10 | % | Plasticizer, Oil Component |
| Decyl Cocoate | 5-9 | % | Plasticizer, Oil Component |
| Paraffinum Liquidum | 4-8 | % | Oil Component, Skin protection agent against aqueous media |
| Glycerine 85% | 1-4 | % | Moistener/Moisturizer |
| Cetyl PEG/PPG-10/1 Dimethicone | 0.5-4 | % | Emulsifier |
| *Prunus Amygdalus Dulcis* (Almond) Oil | 0.5-4 | % | Plasticizer, Moisturizer/Care Component |
| Polyglyceryl-4 Isostearate | 0.5-4 | % | Emulsifier |
| Potassium Sorbate Sodium Benzoate | 0.5-2 | % | Preservative |
| Citric Acid | 0.5-4 | % | pH Regulator |
| Sodium Hydroxide 50% | 0.2-0.8 | % | pH Regulator |
| Creatine | 0.3-0.7 | % | Moisturizer |
| Sodium Chloride | 0.3-0.7 | % | Viscosity increasing agent |
| Perfume (Fragrance) | 0.3-0.7 | % | Fragrance |
| Hydrogenated Castor Oil | 0.3-0.7 | % | Consistency Factor |
| Cera Alba (Beeswax) | 0.2-0.6 | % | Consistency Factor, Plasticizer |
| Linseed Oil Fatty Acid | 0.2-0.6 | % | Moisturizer/Oil Component |
| Amino acid Complex | 0.05-0.15 | % | Moistener/Protein Builder |
| *Rosmarinus Officinalis* (Rosemary) Leaf Extract | 0.005-0.015 | % | Antioxidant |
| Tocopherol | 0.001-0.004 | % | Vit. E/Antioxidant/Moisturizer |

The weight contents of the individual components are adjusted such that in total 100% by weight are yielded.

Procedural Instruction a) Fatty Phase with Zinc Oxide

Tocopherol, rosemary extract, linseed oil fatty acid are distilled, hydrogenated castor oil, cera alba, polyglyceryl-4 isostearate, cetyl PEG/PPG-10/1 dimethicone, almond oil, fluid paraffin, decyl cocoate, and cethyl ethyl hexanoate are first added into the Fryma and heated to 85° C. At the stirrer adjustment of 10 rpm all raw materials are melted, and the temperature is maintained for about 15 min. After the homogenizer zinc oxide is put into the Fryma with 1200 rpm and homogenized: 3 min./2000 r.

b) Water Phase

The Unimix is sterilized with the minimum amount of water necessary (ca. 150 kg); subsequently it is cooled to 55° C. One part of hot water is let out for the pre-solutions: sodium chloride, citric acid are dissolved in the hot water. Sodium hydroxide solution, 50%, is dissolved in the hot water. Amino acid complex, glycerol, 85%, are dissolved in the hot water. Potassium sorbate is dissolved in the hot water. Residual water, purified—except 10%—is put into the Unimix. Stirrer 30 rpm. The pre-solutions are put into the Unimix and well stirred until a homogeneous solution is obtained (ca. 2 min./1400 r).

Then, creatine is put in and the remaining 10% water, purified, are also added. Homogenization within 2 min. at 1400 r. The pH value is controlled (set point 4.8-5.1).

c) Perfume Oil Phase

The perfume oil is weighted and provided.

d) Emulsification

The cold water phase is put into the Fryma to the hot fatty phase under stirring (20 rpm). Cooling is started with running stirrer (20 rpm). Homogenization: 5 min./2200 r. Vacuum is released. At 35° C. the perfume oil is allowed to enter. It is homogenized for ½ min. at 1200 r. Up to 30° C. it is cooled under stirring. Then, homogenization: 6 min./4100 r. (at 1,500 kg batch size). Up to 29° C. it is cooled under stirring. Compressed air is build up (1 bar). At 29° C. the cream is pumped into a sterile storage tank by means of compressed air (1 bar) and with a homogenizer performance of 2000 to 3000 r. Here, the vacuum is released.

Example 3

Formulation 3: Transparent Skin Protection Cream (W/O/W Emulsion)

| | | | |
|---|---|---|---|
| Aqua (Water) | 60-80 | % | Solvent (Vehicle) |
| PARAFFINUM LIQUIDUM | 4-8 | % | Oil Component, Skin protection agent against aqueous media |
| ISOPROPYL PALMITATE | 1-4 | % | Plasticizer |
| CETEARYL ALCOHOL | 1-4 | % | Viscosity increasing agent |
| POLYGLYCERYL-2 DIPOLYHYDROXYSTEARATE | 1-4 | % | Skin Conditioning |
| PROPYLENE GLYCOL | 1-4 | % | Solubilizer, Moistener |
| CETEARYL GLUCOSIDE | 1-4 | % | Emulsification |
| C 12-15 ALKYL BENZOATE | 1-4 | % | Plasticizer, Skin Conditioner, Fat Component |
| STEARIC ACID | 0.5-3 | % | Matrix forming agent, Emulsifier |
| PETROLATUM | 0.5-3 | % | Skin Protection Agent |
| BISABOLOL | 0.5-3 | % | Skin-care Product |
| PHENOXYETHANOL | 0.5-1.5 | % | Preservative |
| PEG-30 DIPOLYHYDROXYSTEARATE | 0.1-0.8 | % | Emulsifier |
| PEG-40 STEARATE | 0.1-0.8 | % | Emulsifier |
| CREATINE | 0.05-0.15 | % | Moisturizer |
| *PRUNUS AMYGDALUS DULCIS* OIL | 0.1-0.8 | % | Plasticizer, Moisturizer/Care Component |
| LINSEED OIL FATTY ACID | 0.05-0.15 | % | Moisturizer/Oil Component |
| PERFUME (FRAGRANCE) | 0.05-0.4 | % | Fragrance |
| *ROSMARINUS OFFICINALIS* LEAF EXTRACT | 0.01-0.05 | % | Antioxidant |
| METHYLPARABENE | 0.1-0.5 | % | Preservative |
| PROPYLPARABENE | 0.01-0.04 | % | Preservative |
| ETHYLPARABENE | 0.01-0.05 | % | Preservative |
| ISOBUTYLPARABENE | 0.005-0.03 | % | Preservative |
| BUTYLPARABENE | 0.01-0.05 | % | Preservative |
| AMINO ACID COMPLEX | 0.05-0.15 | % | Moistener/Protein builder/ |

The weight contents of the individual components are adjusted such that in total 100% by weight are yielded.

Procedural Instruction a) Water Phase

Demineralized water is first added and creatine, propylene glycol, PEG 40 stearate and amino acids are dispersed therein. The phase is heated to 80° C., subsequently a mixture of phenoxyethanol, methylparabene, butylparabene, ethylparabene, propylparabene, and isobutylparabene is added and homogeneously dispersed.

b) Fatty Phase

Sequentially, cetearyl glucoside, polyglyceryl-2 dipolyhydroxystearate, PEG-30 dipolyhydroxystearate, paraffinum liquidum, petrolatum, isopropyl palmitate, C12-C15 alkyl benzoate, cetearyl alcohol, and stearic acid, almond oil, linseed oil fatty acid, and *Rosmarinus Officinalis* leaf extract are first added, melted at 80° C. and homogeneously mixed. Last, at 80° C. bisabolol is added and homogeneously stirred in.

c) Perfume Oil Phase

The perfume oil is weighted and provided.

d) Emulsification

The 80° C. hot fatty phase is subsequently transferred into the 80° C. hot water phase and homogeneously stirred in. Under vacuum it is post-stirred and subsequently homogenized. Under stirring it is cooled below 30° C. Finally, the perfume oil is stirred in and the product is filled.

Example 4

Formulation 4: Skin Protector (Foam)

| | | | |
|---|---|---|---|
| Aqua (Water) | 60-80 | % | Solvent |
| Butane | 4-8 | % | Propellant |
| Urea | 2-6 | % | Moistener, Moisturizer |
| Stearic Acid | 2-6 | % | Matrix Forming Agent, Emulsifier |
| Octyl Palmitate | 1-4 | % | Solvent/Carrier/Plasticizer/Fragrance Fixing Agent |
| Propane | 1-4 | % | Propellant |
| Isobutane | 1-4 | % | Propellant |
| Palmitic Acid | 0.5-1.5 | % | Opacifier/Emulsifier |
| Myristic Acid | 0.5-1.5 | % | Opacifier/Tenside |
| Sodium Lauryl Sulphate/Sodium Myristyl Sulphate/Sodium Cetyl Sulphate/Sodium Stearyl Sulphate/Laureth 10 | 0.5-1.5 | % | Opacifier/mother-of-pearl Pigment |
| Lecithin | 0.5-1.5 | % | Oil Component, Oil Regenerating/Regreasing Agent (Plasticizer) |
| Mineral Oil | 0.5-1.5 | % | |
| Alcohol | 0.5-1.5 | % | Skin Cooling Agent; Preservative |
| Ethanol Amine | 0.2-0.8 | % | Emulsifier/pH regulator |
| Panthenol | 0.2-0.8 | % | Moistener (Moisturizer) |
| *Prunus Dulcis* Oil | 0.2-0.8 | % | Plasticizer, Moisturizer/Care Product |
| Linseed Oil Fatty Acid | 0.2-0.8 | % | Moisturizer/Oil Component |
| Creatine | 0.2-0.8 | % | Moisturizer |
| Aminomethyl Propanol | 0.2-0.8 | % | pH Regulator |
| Propylene Glycol | 0.38 | % | Solubilizer, Moistener |
| Sorbitane Trioleate | 0.05-0.15 | % | Emulsifier |
| Oleic Acid | 0.005-0.15 | % | Tenside/Moisturizer |
| Amino Acids | 0.005-0.15 | % | Moistener/Protein Builder |
| Glycerine | 0.005-0.15 | % | Moistener, Moisturizer |
| Cocamide MEA | 0.01-0.09 | % | Foam-stabilizing and Consistency-imparting Agent |

The individual components of the foam are selected such that in total 100% by weight are yielded.

Procedural Instruction:
1. Cocamide MEA, stearic acid, palmitic acid, oleic acid, and myristic acid are melted at approx. 60-70° C. (pre-charge 1).
2. Demineralized water, ammonium methylpropanol, ethanol amine, glycerin, and a mixture of sodium lauryl sulphate, sodium myristyl sulphate, sodium cetyl sulphate, sodium stearyl sulphate, and laureth 10 are heated to approx. 60-70° C. (pre-charge 2).
3. The melt of pre-charge 1 is added to the hot water via a sieve (pre-charge 2) and well stirred.
4. Cooling to 40° C.
5. Subsequently, the residual raw materials amino acids, linseed oil and almond oil are added under stirring.
6. Finally, lecithin and alcohol are added.
7. Filling is performed on a specific aerosol filling line. The aerosol cans are filled with 86 g ±1.7 g of the active ingredient emulsion. The aerosol cans are provided with valve and crimped. Then, propane/butane at 9.5 g±0.5 g are filled through the valve. Subsequently, the cans are loaded with 7 bar of nitrogen.

Example 5

Evidence of Effectiveness

1. In vitro Reconstruction of Humane Epidermis—Histological Study

Figure 1:
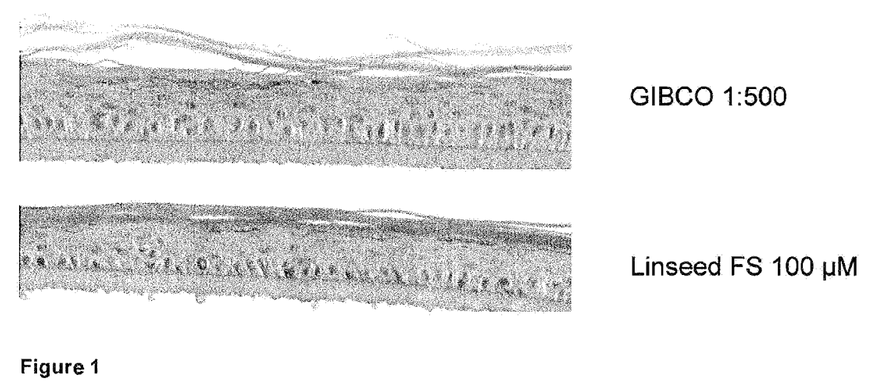
FIG. 1 shows the morphology of in vitro reconstructed epidermis after 14 days. The upper cell layer was grown without linseed oil fatty acids, the lower one in the presence of 100 mM of linseed oil fatty acids.

The examination of the effectiveness of cosmetic products meets with different difficulties. For ethical reasons, many experiments in humans cannot be performed. Also the use of animals for testing cosmetics meets with significant oppositions. Thus, in the present invention an in vitro system was used in which human primary keratinocytes were grown on a polycarbonate filter membrane, wherein the common growth factors and additives were added. First, the cells were grown submersed for about 4-5 days and then, contacted with the air/liquid interphase. The cell cultures were grown once with and once without the linseed oil fatty acids in a standard growth medium (GIBCO). Here, in the histological section a significant difference was observed. In both cases, a differentiation of the basal cells was observed, but the cell structure formed in the linseed oil fatty acid-containing growth medium is more compact. FIG. 1 shows the morphology of in vitro reconstructed epidermis after 14 days. The upper cell layer was grown without linseed oil fatty acids, the lower one in the presence of 100 μM of linseed oil fatty acids.

Transferring the effect observed in the in vitro model to the application on aging skin results in the formation of a compact skin structure that is advantageous to permit a supply of the outermost skin layers with moisture from the inside. The improvement of the barrier effect of the active ingredient complex on the aging skin is mainly caused by the linseed oil fatty acids.

Example 6

As described in example 5, keratinocytes were grown. The cells were exposed to stress by adding a detergent (1% aqueous solution Triton X-100). Also here, the viability of the cells once grown in the presence of linseed oil fatty acid (100 μM) was compared with cells grown in growth media without linseed oil fatty acid (GIBCO).

Figure 2:
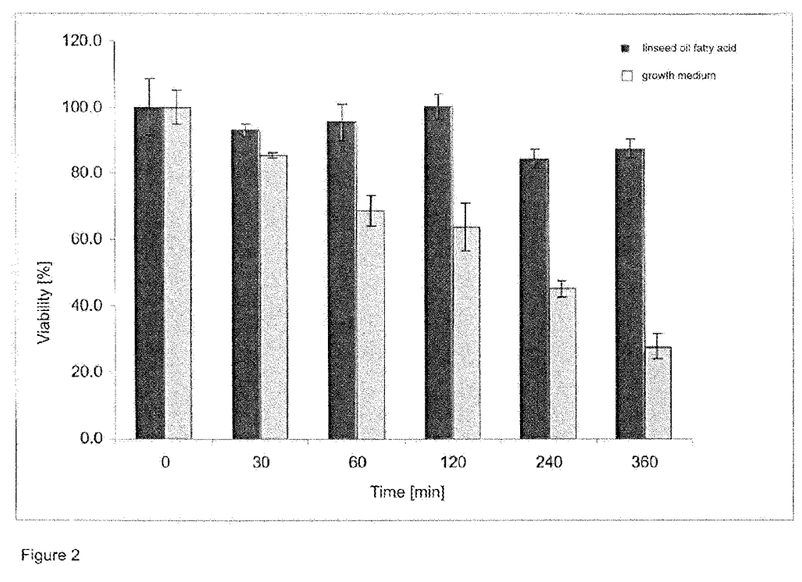
FIG. 2 compares the viability of keratinocytes grown in the presence of linseed oil fatty acid (100 μM) to those grown in a growth media without linseed oil fatty acid (GIBCO) upon exposure to a detergent (1% aqueous solution Triton X-100). As the depicted results demonstrate, the cells from the linseed oil fatty acid-containing growth medium were substantially more robust than the cells from the standard growth media. See Example 6.

If the reconstructed cells are exposed to a detergent, so a significant loss of the viability of those cells (>50%) that are differentiated in the standard growth medium is observed after 240 minutes, whereas the cells from a linseed oil fatty acid-containing growth medium are substantially more robust over the detergent and do not show a significant reduction of the viability, not even after 360 minutes. The results are represented in FIG. 2.

Example 7

Protection of the Skin from Aqueous Harmful Substances

Formulations 1 to 4 were tested in 16 test persons with healthy skin. The control was a 2.5% solution of sodium lauryl sulphate on untreated skin without a skin protection agent.

Test Description:

Day 1 to Day 4
- a) visual evaluation of the skin damage and Tewl measurements in the individual test fields
- b) application of the test products to the test fields, 5 minutes exposure time
- c) occlusive application of the harmful substance in Finn chambers for 30 minutes
- d) repetition of steps b) and c) after 2-3 hours Day 5 only visual evaluation and TEWL measurements (TEWL=transepidermal water loss)

Figure 3:
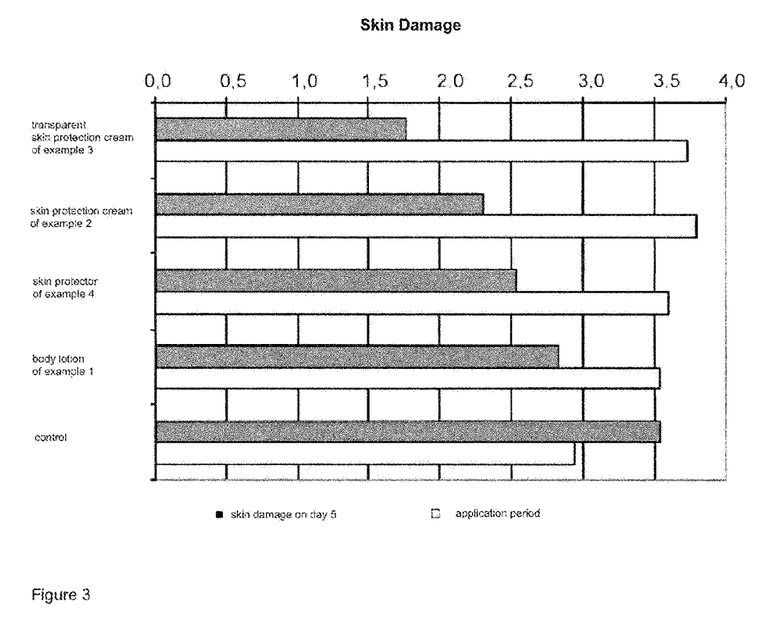
FIG. 3 demonstrates the protective effect of the test formulations of Examples 1 to 4 from skin damage brought on by sodium lauryl sulfate (SLS). As the depicted results demonstrate, skin damage was lower in all test fields with the test formulations of Examples 1 to 4 as compared to the control. See Example 7(a).

A classification of the skin damage is in reddening and scaling of the skin as well as formation of fissures. All three characteristics are judged in relation to the control. The classification is in steps of 0.5, where the value "0" means that no skin damage has occurred. The values of reddening, scaling, and fissures are added. The test is terminated for a certain test field if for ethical reasons a further skin damage of the test person can no longer be justified (added value of the skin damage of ca. 2-3). Therefore, the application period of a product is included in the evaluation.

a) Results of the Visual Evaluation:

All formulations 1 to 4 have protected from a damaging effect of the sodium lauryl sulphate. In all test fields with formulations 1 to 4 the skin damage was lower than with the control value. This correlates with a longer application period of the products over sodium lauryl sulphate. The highest protection in this test was caused by the transparent skin protection cream (formulation 3). The results are represented in FIG. 3.

b) Results of the Trans-Epidermal Water Loss (TEWL):

The measurements of the trans-epidermal water loss (TEWL) were carried out with probes of Courage & Khazaka, Köln. In the test fields where the test was earlier terminated the end values have been determined by means of a linear regression.

Figure 4:
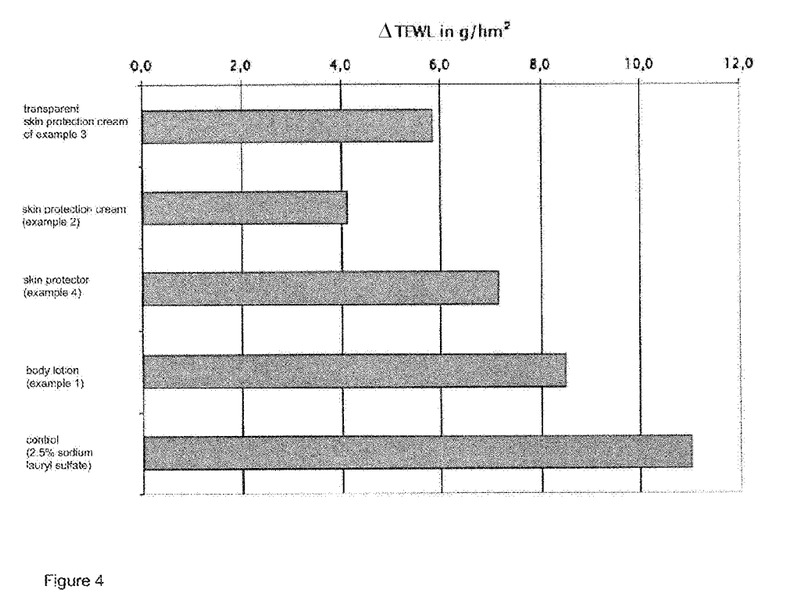
FIG. 4 presents the results of a trans-epidermal water loss (TEWL) assay on the test formulations of Examples 1 to 4 and a control value (2.5% SLS). As the depicted results demonstrate, all test formulations were able to limit the barrier damage brought on by SLS exposure. See Example 7(b).

The standard harmful substance sodium lauryl sulfate causes a barrier damage of the skin that results in an increased vaporization of water through the uppermost skin layers. On average, this value increases by 11 g/hm$^2$. In all tested formulations 1 to 4 this increase is lower. The change in trans-epidermal water loss in the formulations 1 to 4 is below 10 g/hm$^2$, in particular between 3 g/hm$^2$ and 9 g/hm$^2$. The least barrier damage of the skin is caused by the pretreatment with skin protection cream (formulation 2); the change in trans-epidermal water loss is about 4 g/hm$^2$.

The results of the experiment are represented in FIG. 4.

Formulations 1 to 4 all show a protective effect over aqueous harmful substances, tested in the model harmful substance sodium lauryl sulphate. In the visual evaluation markedly less skin damages occurred than in the control value. The barrier function of the skin could be better maintained by the use of the mentioned product in comparison with the standard. The transparent skin protection cream (formulation 3) and the skin protection cream (formulation 2) proved particularly effective.

Example 8

Study of the Interaction of the Transparent Skin Protection Cream (Formulation 3) with Incontinence Products In the application of topical protection and care products in humans which are dependent on incontinence products an impairment of the quality of these incontinence products should be avoided. Therefore, at the example of the transparent skin protection cream it was studied how or whether, respectively, it affects the absorption behavior of incontinence products.

The creamed skin contacts the uppermost sheet (top sheet) of the healthcare product that in wearing faces the body. Here is the risk that cream is transferred from the creamed skin to the healthcare product and the permeability of this sheet is negatively affected and this ultimately may lead to premature leakage of the product.

Transfer of the cream is simulated by directly applying a defined amount of the cream according to the invention (formulation 3) and three care products, present on the market, with a varnishing roll of foamed plastic to the area of the distribution system. The incontinence product "Moli-Care Super Premium Air Active Size Medium" of Paul Hartmann AG was used as the test product.

Sample Preparation:

A defined amount of skin-care product (2.5 g=34.72 g/m$^2$) was applied to the incontinence article to a surface area of 18 cm×40 cm (area with distribution system: yellowish cellulose, up to the front edge of the absorbent core=720 cm$^2$). An untreated product is used as a blank.

With a 11 cm varnishing foamed plastic roll a defined amount of a skin-care product is distributed over the predetermined contact area of the incontinence article and intermingled (here, it is important to ensure that no cream nests are formed). Application with the varnishing foamed plastic roll results in a very uniform distribution of the skin-care product, even with low application amounts.

1. Run-off Test:

The incontinence article is stretched over an inclined plane. At the upper end for two times a defined amount of a test liquid is added via a feed hopper. At the lower end the beading amount of liquid is collected and weighted.

2. Soak in Times (Acquisition Time)/Rewet Test:

The incontinence article is placed on a body adapted test apparatus (KANGA Inko) such that the treated area of the article is centered to point of addition, (lateral load: 4.5 kg) The test apparatus is laterally placed with the bottom onto a ramp having an inclination of 35° (following the Absorption Before Leakage (ABL-) test of EDANA). Here, the lower lateral edge must lie on the horizontal ground area. Via the addition tube 100 ml of a 0.9% NaCl solution (colored) are added and the acquisition time is measured. This is repeated three times (total amount of liquid: 300 ml) each with a delay between the additions of 10 minutes.

Figure 5:
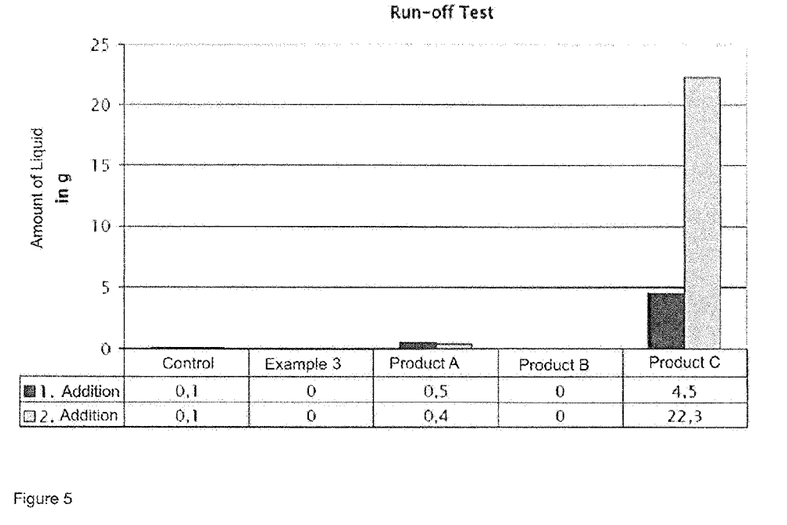
FIG. 5 presents the results of a run-off test comparing the transparent skin protection cream of Example 3 to three competitive products A, B, and C. See Example 8(a).
Figure 6:
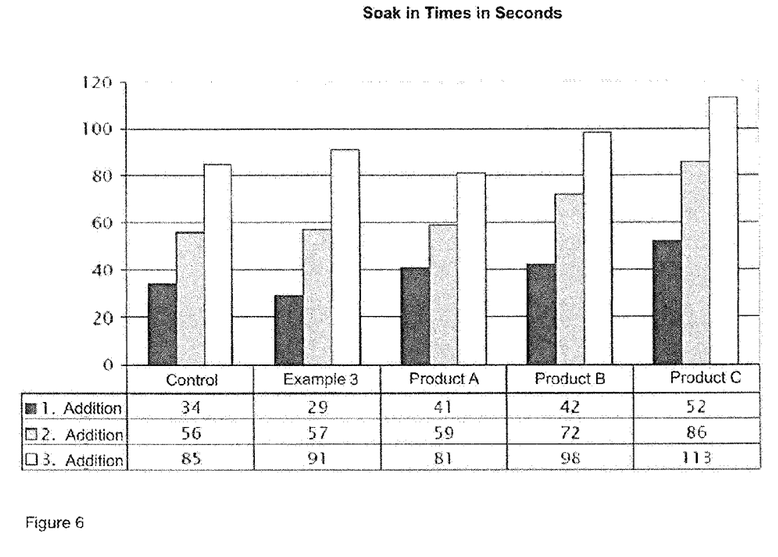
FIG. 6 presents the results of a soak time assay comparing the transparent skin protection cream of Example 3 to three competitive products A, B, and C. See Example 8(b).
Figure 7:
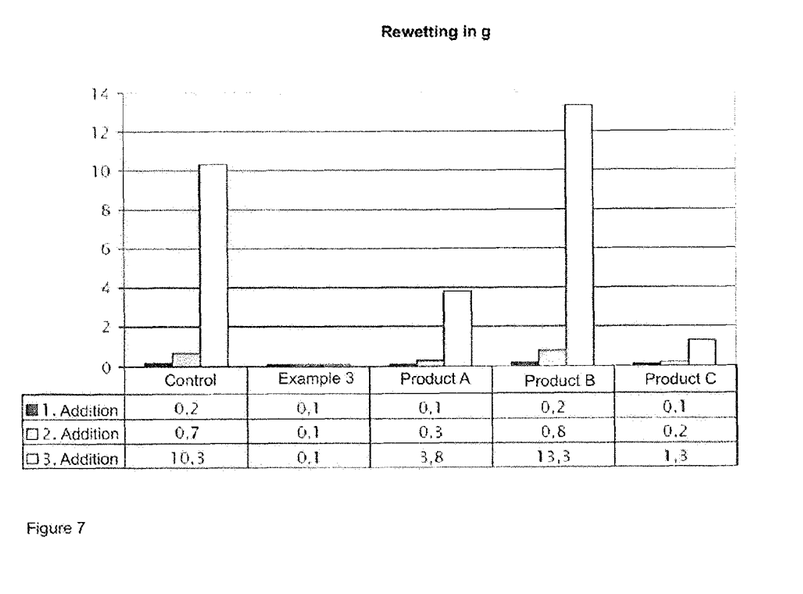
FIG. 7 presents the results of a rewetting assay comparing the transparent skin protection cream of Example 3 to three competitive products A, B, and C. See Example 8(c).

After each delay the incontinence article is taken out of the KANGA and laid flat on a tabletop. Approx. 40 g filter paper (Macherey-Nagel MN617, diameter 90 mm) are centrally placed on the point of addition of the incontinence article and loaded with a weight of 1,270 g for 5 minutes. Subsequently, the filter stack is reweighted and so, rewetting is determined.

a) Results of the Run-Off Test:

The control measurement yields a minimum amount of liquid beading from the untreated top sheet. The transparent skin protection cream does not increase this amount, accordingly does not affect the quality of the incontinence product. Also, three competitive products were tested only one of which (product B) had no influence on the Run-off value. Product A resulted in a slight increase, product C in a very strong increase of the amount of liquid and thus in an increased risk of premature leakage of the healthcare product. The results are represented in FIG. 5.

b) Results Soak in Times:

In comparison with a control measurement an incontinence product treated with transparent skin protection cream shows an only slightly longer 3rd soak in time. In the nappies treated with products B and C all three additions result in markedly longer times the liquid requires for penetration. The results are represented in FIG. 6.

c) Results Rewet:

In the control measurements the amount of liquid not absorbed by the incontinence product increases at each addition. This tendency is also observed in all competitive products A, B, C, but not in the composition of the transparent skin protection cream (formulation 3) according to the invention. In fact, products A and C also reduce the delivered amount of the test liquid, but only the composition in accordance with formulation 3 according to the invention almost completely prevents rewetting. This is represented in FIG. 7.

d) Summary

On the example of the transparent skin protection cream it could be shown that the compositions according to the invention have no negative influence on the quality of the tested incontinence products, proven with Run-off tests and measurements of soak in times and rewetting. Moreover, it could be shown that the rewetting properties of the incontinence products are positively affected such that rewetting is almost completely absent. In turn, this positively affects the skin condition of those parts of skin getting in touch with the incontinence article.

Example 9

Practice Test

In a practice test formulations 1, 3 and 4 were tested by 90 examined geriatric nurses in 270 occupants of retirement/nursing/handicapped persons' homes, wherein each geriatric nurse treated three occupants with the products, wherein at least two of the occupants suffered from at least slight incontinence and were cared for with healthcare products for several times a week already before the start of the practice test. 64% of the attending home occupants suffered from problematic skin conditions.

In the practice test the groups to be studied were formed such that either the foam or the transparent skin protection cream in combination with the body lotion was used. During the two-week test period further non-inventive products were applied, in particular for cleaning (washing lotion, caring bath, shampoo, cleaning foam, baby wipes), but also to protect (oily skin protection spray) and care of the skin (skin fluid gel, care oil, hand cream).

Both the moisturizing effect and the protective effect, the caring effect and skin tolerance of the studied products in more than 92% of all cases were rated good to very good. It was found that during the first week of application the skin condition in 63% of the home occupants was markedly improved and after two weeks of the application period in 71% of the home occupants the skin condition was improved. Here, it was asked for the skin conditions: dry, fissured/scaling, itching, reddened, papyraceous.

The invention claimed is:

1. A medicinal skin protection composition containing an active ingredient combination that improves the barrier function of aging skin, wherein said medicinal skin protection composition takes the form of a water-in-oil emulsion (W/O) or a water-in-oil-in-water emulsion (W/O/W), further wherein said active ingredient combination consists of Composition A consisting of the following components:
a) 0.01 to 20% by weight of almond oil,
b) 0.01 to 1.5% by weight of linseed oil fatty acids,
c) 0.001 to 0.5% by weight of amino acids, and
d) 0.01 to 1.5% by weight of creatine, or, alternatively
said active ingredient combination consists of Composition B consisting of the following components:
a) 0.1 to 15% by weight of almond oil,
b) 0.05 to 0.8% by weight of fatty acids of vegetable origin with an omega6 to omega3 fatty acid ratio of 1 to >1,
c) 0.005 to 0.15% by weight of amino acids selected from the group consisting of arginine (Arg), glutamine (Gln), histidine (His), serine (Ser) and combination thereof and/or at least one natural moisturizing factor,
d) 0.05 to 0.8% by weight of creatine,
wherein the recited weight percentages each relate to the weight of the total composition.

2. The medicinal skin protection composition according to claim 1, wherein said almond oil of Composition A or B comprises 70-80 wt % oleic acid, 10-20 wt % linoleic acid and 5-10 wt % palmitic acid, wherein the recited weight percentages each relate to the weight of the total composition.

3. The medicinal skin protection composition according to claim 1, wherein said linseed oil fatty acids of Composition A comprise a mixture of saturated, unsaturated and polyunsaturated fatty acids.

4. The medicinal skin protection composition according to claim 1, characterized in that the amino acids of Composition A are selected from the group consisting of arginine (Arg), glutamine (Gln), histidine (His), serine (Ser), and combinations thereof and/or at least one natural moisturizing factor selected from the group consisting of pyrrolidine carboxylic acid (PCA) and/or urocanic acid (UCA).

5. The medicinal skin protection composition according to claim 1, characterized in that said medicinal skin protection composition comprises a water-in-oil emulsion in the form of a body lotion containing 1.0 to 25% by weight of the active ingredient combination, based on the weight of the total composition, further wherein the ratio of amino acids: linseed oil fatty acids:creatine:almond oil ranges from 0.5:2:4:100 to 0.5:4:5:100.

6. The medicinal skin protection composition according to claim 1, characterized in that said medicinal skin protection composition comprises a water-in-oil emulsion in the form of a skin protection cream containing 0.5 to 8.0% by weight of the active ingredient combination, based on the weight of the total composition, further wherein the ratio of the components of the active ingredient combination amino acids:linseed fatty acids:creatine:almond oil ranges from 0.5:4:6:10 to 0.5:4:5:27.

7. The medicinal skin protection composition according to claim 1, characterized in that said medicinal skin protection composition comprises a water-in-oil-in-water emulsion in the form of a transparent skin protection cream containing 0.05 to 2.0% by weight of the active ingredient combination, based on the weight of the total composition, further wherein the ratio of the components amino acids: linseed fatty acids:creatine:almond oil ranges from 0.5:1:1:2 to 0.5:1:1:5.

8. The medicinal skin protection composition according to claim 1, characterized in that said medicinal skin protection composition comprises a foam having 0.1 to 4.0% by weight of the active ingredient combination, based on the weight of the total composition, further wherein the ratio of the components amino acids:linseed oil fatty acids:creatine:almond oil ranges from 0.0125:1:1:1 to 0.125:1:1:1.

9. A method of treating aging skin in a subject in need thereof, said method comprising the step of topically applying the medicinal skin protection composition according to claim 1 to the aging skin of said subject.

10. The method according to claim 9, wherein the aging skin of said subject is strained by one of more of bed confinement, urinary and/or fecal incontinence, decubitus and other wound disease.

11. The method according to claim 9, wherein said medicinal skin protection composition is applied to the whole body or, alternatively, is restricted to perilesional skin, genitals strained by incontinence, or both.

12. The method according to claim 9, wherein said medicinal skin protection composition is combined with an absorbent healthcare product.

13. The medicinal skin protection composition according to claim 1, wherein said composition is formulated for the topical application to aging skin strained by bed confinement, urinary and/or fecal incontinence, decubitus and/or other wound disease.

14. The medicinal skin protection composition according to claim 1, wherein said composition is combined with an absorbent healthcare product selected from the group consisting of incontinence articles, primary wound dressings, and patient under pads for application to aging skin of the whole body, perilesional skin, the genitals or combinations thereof.

15. An absorbent healthcare article having a free side and a side that faces the skin of the user, wherein said user-facing side is provided with a coating that includes the medicinal skin protection composition according to claim 1.

16. The medicinal skin protection composition according to claim 1, wherein said at least one natural moisturizing factor of Composition B comprises pyrrolidine carboxylic acid (PCA), urocanic acid (UCA), or a combination thereof.

17. The medicinal skin protection composition of claim 3, wherein said linseed oil fatty acids of Composition A comprises:
4-8 wt % palmitic acid,
2-5 wt % stearic acid,
16-26 wt % oleic acid,
14-24 wt % linoleic acid,
43-55 wt % linolenic acid, and
0.1-2 wt % fatty acids with carbon chains having more than 18 carbon atoms
wherein the recited weight percentages each relate to the total composition.

18. The medicinal skin protection composition according to claim 5, characterized in that said body lotion contains 2.5 to 20% by weight of the active ingredient combination, based on the weight of the total composition.

19. The medicinal skin protection composition according to claim 5, characterized in that said body lotion contains 5.0 to 18% by weight of the active ingredient combination, based on the weight of the total composition.

20. The medicinal skin protection composition according to claim 6, characterized in that said skin protection cream contains 0.75 to 7.0% by weight of the active ingredient combination, based on the weight of the total composition.

21. The medicinal skin protection composition according to claim 6, characterized in that said skin protection cream contains 1.0 to 6.0% by weight of the active ingredient combination, based on the weight of the total composition.

22. The medicinal skin protection composition according to claim 7, characterized in that said transparent skin protection cream contains 0.1 to 1.7% by weight of the active ingredient combination, based on the weight of the total composition.

23. The medicinal skin protection composition according to claim 7, characterized in that said transparent skin protection cream contains 0.2 to 1.3% by weight of the active ingredient combination, based on the weight of the total composition.

24. The medicinal skin protection composition according to claim 8, characterized in that said foam contains 0.2 to 3.5% by weight of the active ingredient combination, based on the weight of the total composition.

25. The medicinal skin protection composition according to claim 8, characterized in that said foam contains 0.5 to 3.0% by weight of the active ingredient combination, based on the weight of the total composition.

26. The method according to claim 12, wherein said absorbent healthcare product is selected from the group consisting of incontinence articles, primary wound dressings, and patient under pads.

* * * * *

UNITED STATES PATENT AND TRADEMARK OFFICE
CERTIFICATE OF CORRECTION

PATENT NO. : 9,849,079 B2  
APPLICATION NO. : 14/239345  
DATED : December 26, 2017  
INVENTOR(S) : Hans Smola et al.

Page 1 of 1

It is certified that error appears in the above-identified patent and that said Letters Patent is hereby corrected as shown below:

On the Title Page

Under the heading "Assignees", at item (73), Line 2, kindly delete the phrase "Evonik Industrie AG, Krefeld (DE)" and replace it with -- Deb IP Limited, Denby (UK) --.

Signed and Sealed this  
Twenty-first Day of August, 2018

Andrei Iancu  
*Director of the United States Patent and Trademark Office*